United States Patent [19]

Imai

[11] Patent Number: 4,465,885
[45] Date of Patent: Aug. 14, 1984

[54] SOLID PHOSPHORUS FLUORIDE CATALYSTS

[75] Inventor: Tamotsu Imai, Mount Prospect, Ill.

[73] Assignee: UOP Inc., Des Plaines, Ill.

[21] Appl. No.: 512,275

[22] Filed: Jul. 8, 1983

[51] Int. Cl.$^3$ .......................... C07C 2/68; C07C 2/02
[52] U.S. Cl. ...................................... 585/466; 585/529
[58] Field of Search ................................ 585/466, 529

[56] References Cited

U.S. PATENT DOCUMENTS 4,288,647  9/1981  Chu ...................................... 585/466
4,356,338 10/1982  Young .................................. 585/466

Primary Examiner—Curtis R. Davis
Attorney, Agent, or Firm—James R. Hoatson, Jr.; Raymond H. Nelson; William H. Page, II

[57] ABSTRACT

Olefinic hydrocarbons which contain from three to about six carbon atoms may be subjected to oligomerization reactions as well as being used as alkylating agents in the alkylation of alkylatable hydrocarbons by treatment at reaction conditions in the presence of a catalyst comprising a phosphorus fluoride such as phosphorus trifluoride or phosphorus pentafluoride composited on a high surface area metal oxide such as gamma-alumina. The oligomers which are obtained in the oligomerization process will contain less branching than those which are obtained when utilizing other catalysts.

9 Claims, No Drawings

SOLID PHOSPHORUS FLUORIDE CATALYSTS

BRIEF SUMMARY OF THE INVENTION

Many olefinic hydrocarbons which contain from 4 to about 12 carbon atoms in the chain are utilized in various industries in many ways. In addition, alkylated hydrocarbons such as alkyl aromatics will also find a wide variety of uses. For example, one specific use of olefinic hydrocarbons such as those containing 8 carbon atoms in the chain is as a component in motor fuels such as internal combustion engines utilizing gasoline. The presence of these compounds in the motor fuel will improve the octane number of the fuel to a higher level, thus enabling the motor fuel such as gasoline to operate efficiently at this high octane number, either in the leaded or unleaded state. Another use of compounds such as the $C_8$ olefinic hydrocarbons would be as plasticizers, especially those olefinic hydrocarbons which possess a relatively straight chain configuration with a minimum of branching, such as only one or two methyl substituents on the chain. The use of these compounds as plasticizers which, when added to a plastic, will facilitate the compound as well as improve the flexibility and other properties of the finished product. Examples of uses for olefinic hydrocarbons containing 6 carbon atoms would be in the synthesis of flavors, perfumes, medicines, dyes and resins, while olefinic hydrocarbons containing 12 carbon atoms in the chain may be used as intermediates in the preparation of detergents, lubricants, additives, plasticizers as well as in the synthesis of flavors, perfumes, medicines, oils, dyes, etc. In a like manner, alkyl aromatic compounds which have been prepared by the alkylation of aromatics such as benzene, toluene, etc. with an olefinic hydrocarbon precursor are also useful in many ways. For example, ethylbenzene will find use in organic synthesis, as a solvent or diluent as well as an intermediate in the production of styrene. Butylated benzenes such as tertbutylbenzene may be used in the synthesis of dyes, pharmaceuticals and other organic chemicals as well as in the manufacture of resins. Cymene (isopropyltoluene) is used as a solvent in metal polishers, in organic syntheses reactions, etc.

The preparation of the oligomerized olefinic hydrocarbons or the alkylation of alkylatable aromatic hydrocarbons as well as other reactions such as skeletal isomerization, double bond migration of olefins, etc. may be effected in the presence of a catalytic composition of matter of a type hereinafter set forth in greater detail.

It is therefore an object of this invention to provide a catalytic composition of matter which is useful for effecting the desired chemical reactions.

A further object of this invention is to provide a solid catalytic composition of matter which may be utilized to prepare products having a desired skeletal configuration.

In one aspect, an embodiment of this invention resides in a catalytic composition of matter comprising a phosphorus fluoride composited on a high surface area metal oxide support.

Another embodiment of this invention is found in a process for the preparation of a catalytic composition of matter which comprises contacting a high surface area metal oxide support with a phosphorus fluoride at contact conditions, calcining and recovering the resultant composite.

A specific embodiment of this invention resides in a catalytic composition of matter comprising phosphorus pentafluoride composited on gamma-alumina.

Another specific embodiment of this invention is found in a process for the preparation of a catalytic composition of matter which comprises contacting gamma-alumina with phosphorus pentafluoride at a temperature in the range of from about 100° to about 350° C., calcining the resultant composite at a temperature in the range of from about 350° to about 600° C. and recovering the resultant catalytic composition of matter.

Other objects and embodiments will be found in the following detailed description of the present invention.

DETAILED DESCRIPTION OF THE INVENTION

As hereinbefore set forth, the present invention is concerned with a catalytic composition of matter and to a process for preparing the composite. The catalyst comprises a solid support, and preferably a high surface area metal oxide support having composited thereon a phosphorus fluoride. The metal oxide which is utilized as a base or support for the phosphorus fluoride will comprise a high surface area metal oxide such as alumina and particularly the individual species such as gamma-alumina, eta-alumina, theta-alumina as well as silica or silica-alumina. The term "high surface area" as used in the present specification and appended claims will refer to those metal oxides which possess a surface area ranging from 1 to about 500 $m^2/g$.

The metal oxide supports of the type hereinbefore set forth will have impregnated thereon a phosphorus fluoride. In the preferred embodiment of the invention the compounds which are used to impregnate the support and thus afford the desired phosphorus fluoride will comprise phosphorus trifluoride or phosphorus pentafluoride. However, it is also contemplated within the scope of this invention that other phosphorus fluoride compounds which will decompose at elevated temperatures to provide the necessary components may also be used, although not necessarily with equivalent results. Examples of such compounds which may be employed will include phosphorus chlorofluoride, phosphorus oxyfluoride, phosphorus thiofluoride, etc.

The catalyst composite of the present invention may be prepared by drying the high surface area metal oxide support for a period of time sufficient to effect a dehydration of the support. Following this, the dried or calcined support may then be placed in an appropriate apparatus such as an autoclave of the rotating, mixing or stirring type and the autoclave is purged with a substantially inert gas such as nitrogen. After heating the apparatus to the desired temperature which may range from about 100° to about 300° C., the phosphorus fluoride compound, in gaseous form, is charged to the reactor. The reaction is then allowed to proceed for a predetermined period of time which may range from about 0.5 up to about 10 hours or more in duration, following which the autoclave is again purged with an inert gas and allowed to return to room temperature. After return to room temperature and venting any excess pressure, the catalyst composition comprising the phosphorus fluoride composited on the high surface area metal oxide support is recovered and calcined for a period of time which may range from about 400° to about 600° C. The catalyst which is thus prepared will contain from about 1% to about 15% of fluorine and from about 1 to about 4 hours at a temperature in the range of from about 400° to about 600° C. The catalyst which is thus prepared will contain from about 1% to about 15% of fluorine and from about 0.5% to about 8% of phosphorus.

As hereinbefore set forth, the catalytic composition of matter which has been prepared according to the process of this invention may be utilized in a wide variety of hydrocarbon conversion reactions including oligomerization, alkylation, skeletal isomerization, double bond migration of olefins, etc. As an illustration of one of the types of reactions, the catalytic composition of matter may be employed in the oligomerization of olefinic hydrocarbons which may contain from about 3 to about 6 carbon atoms or more such as propylene, butene-1, butene-2, pentene-1, pentene-2, hexene-1, hexene-2, hexene-3, etc. The reaction is effected by placing the catalytic composition of matter in an appropriate apparatus such as a reaction flask, pressure-resistant apparatus such as an autoclave, etc. and charging the olefinic hydrocarbon which is to be oligomerized to said apparatus at predetermined reaction conditions which may include a temperature in the range of from about 50° to about 350° C., a pressure in the range of from about 50 to about 2000 psig, and a space velocity which may range from about 0.5 to about 10. If so desired, the olefinic hydrocarbon which is to be oligomerized may be admixed with a paraffin which will act as a diluent for the reaction. Upon completion of the desired reaction period, which may range from about 0.5 up to about 10 hours or more in duration, the reaction mixture, after allowing the apparatus to return to room temperature and atmospheric pressure, is recovered. The desired products comprising the oligomers are separated from the catalyst and unreacted olefins by conventional means such as fractional distillation, decantation, filtration, etc. and recovered.

Another example of a reaction which may be effected employing the catalyst of the present invention is an alkylation reaction in which an alkylatable hydrocarbon such as benzene, toluene, xylene, may be alkylated by contact with an alkylating agent such as an olefinic hydrocarbon containing from 2 to about 14 carbon atoms or more such as ethylene, propylene, butene-1, butene-2, the isomeric pentenes, hexenes, heptenes, octenes, nonenes, decenes, undecenes, dodecenes, tridecenes, tetradecenes, etc; alkyl halides such as ethyl chloride, propyl bromide, isopropyl chloride, n-butyl bromide, secbutyl bromide, etc., in the presence of said catalytic composition of matter. The alkylation reactions may be effected by placing the catalytic composition of matter in an appropriate apparatus such as a reaction flask, autoclave, etc. along with the alkylatable hydrocarbon. The alkylating agent may then be charged to the reactor and the alkylation reaction may be effected at alkylating conditions which will include a temperature in the range of from about 50° to about 300° C. and a pressure ranging from about 50 to about 500 psig. If so desired, the atmospheric pressure which is employed may be provided for by the presence of an inert gas such as nitrogen, argon, helium, etc. in the reaction vessel. Upon completion of the desired residence time, which may also be in a range of from about 0.5 to about 10 hours or more in duration, heating is discontinued and after the reactor has returned to room temperature the excess pressure may be discharged, the autoclave opened and the reaction mixture recovered therefrom. Again, the desired products comprising the alkylated hydrocarbon may be separated from the catalyst and unreacted starting materials by conventional means similar to those hereinbefore set forth, and recovered.

It is also contemplated within the scope of this invention that the reactions involving the use of the catalytic composition of matter of the type hereinbefore described may also be effected in a continuous manner of operation. When this type of operation is employed, a quantity of the catalytic composition of matter is placed in an appropriate apparatus which is maintained at the proper operating conditions of temperature and pressure. The olefinic hydrocarbon which is to be oligomerized either alone or in admixture with a diluent is continuously charged to the apparatus and after contact with the catalyst for a predetermined period of time the reactor effluent is continuously withdrawn and subjected to conventional means of separation whereby the desired oligomers are separated from any unreacted olefins, the former being recovered while the latter is recycled to form a portion of the feedstock.

As will hereinafter be shown in greater detail, the catalytic composition of matter of the present invention will possess an excellent activity for producing oligomers as well as unexpected selectivities. This is particularly illustrated in the fact that the catalyst will have a higher selectivity for trimers and higher oligomers than does a catalyst such as boron trifluoride composited on a high surface area metal oxide support. In addition, the catalyst will also possess a higher selectivity for low-branched isomers and therefore will be suitable for the production of non-gasoline type fuels such as fuels which may be used in diesel or jet engines.

The following examples are given for purposes of illustrating the catalytic composition of matter and a process for preparing the same as well as the use thereof in an oligomerization reaction. However, it is to be understood that these examples are merely illustrative in nature and that the present invention is not necessarily limited thereto.

EXAMPLE I

A catalytic composition of matter of the present invention was prepared by drying 75 grams (150 cc) of gamma-alumina spheres in a muffle furnace for a period of one hour at a temperature of 500° C. in an air atmosphere. The dried base was then loaded into a 500 cc autoclave which was then sealed. The autoclave was purged by charging nitrogen at a rate of one liter per minute for a period of 15 minutes, and thereafter heating of the autoclave was begun. When the internal temperature of the autoclave reached about 100° C., the nitrogen charge was discontinued and phosphorus pentafluoride was charged to the autoclave at a rate of 25 cc per minute until a total of 15.6 grams of the phosphorus pentafluoride had been added. The temperature of the autoclave was raised to 289° C. after a period of one hour and after a period of two hours, a temperature of 322° C. was reached. At the end of the two hour period, the charge of phosphorus pentafluoride to the autoclave was discontinued and a nitrogen purge was instituted. Heating was discontinued and the autoclave and contents thereof were allowed to cool at room temperature. After reaching room temperature, the autoclave was opened and the catalytic composition of matter was recovered and calcined in a quartz tube for a period of two hours at a temperature of 500° C. in a nitrogen atmosphere which was charged to the tube at a rate of one liter per minute. The finished catalyst was analyzed and found to contain 9.5% by weight of fluorine, and 1.9% by weight of phosphorus based on the total catalyst.

EXAMPLE II

To illustrate oligomerization capabilities of the catalyst of the present invention, 28.3 grams of the catalyst prepared according to Example I above was placed in a reactor and a charge comprising 60% butene-2 and 40% n-butane was passed over the catalyst at a Liquid Hourly Space Velocity of 1.0 hrs.$^{-1}$ (based on the butene-2) utilizing a pressure of 1000 psig. During the run which was effected for a period of 36 hours, the inlet temperature of the reactor was 152° C. and the maximum temperature was 172° C.

EXAMPLE III

To illustrate the differences in products which are obtained by using a catalyst prepared according to the process of the present invention compared to a catalyst containing boron fluoride composited on a solid support, a second run was performed in which 28.1 grams of a catalyst comprising 7.05% by weight of fluorine and 1.23% by weight of boron composited on gamma-alumina was placed in a reactor similar to that which was employed in Example II. The feedstock comprising a mixture of 60% butene-2 and 40% n-butane was charged to the reactor at a Liquid Hourly Space Velocity of 1.0 hrs.$^{-1}$ (again based on the butene-2) while maintaining a pressure of 1000 psig. The inlet temperature of the reactor was 136° C. and the maximum temperature was 150° C. After a period of 12 hours, the run was discontinued.

EXAMPLE IV

The reactor effluent from the runs utilizing the catalytic composition of matter of the present invention and the catalyst containing boron fluoride were analyzed, the results being set forth in Table 1 below.

Catalyst "A" is the catalytic composition of matter of the present invention, and catalyst "B" comprises boron fluoride composited on gamma-alumina.

TABLE 1

| Catalyst | A | B |
|---|---|---|
| % Conversion | 60.6 | 60.4 |
| Selectivity, wt. % | | |
| C$_6$ Olefins | 0.8 | 0.8 |
| C$_7$ Olefins | 0.9 | 0.6 |
| C$_8$ Olefins | 61.2 | 79.1 |
| C$_9$+ Olefins | 37.1 | 19.5 |
| Octene Isomers, % | | |
| n-Octene | — | — |
| Methylheptene | 12.2 | 2.8 |
| Dimethylhexene | 87.2 | 96.5 |
| Trimethylpentene | 0.6 | 0.7 |
| Octene Yield, wt. % | 37.1 | 47.8 |

It is obvious from a comparison of the reaction products which are obtained in the oligomerization of butene-2 when utilizing the catalyst of the present invention and a catalyst comprising boron fluoride composited on alumina that the use of the former results in the obtention of products greater than the dimer of butene plus a greater yield of lower branched dimers of butene, said product being useful for diesel or jet fuels.

EXAMPLE V

In a manner similar to that set forth in the above examples, other catalyst compositions may be obtained by drying eta-alumina or theta-alumina bases at a temperature of 500° C. for a period of one hour and thereafter loading the dried spheres in an autoclave. The autoclave may then be sealed and after being purged with nitrogen, phosphorus trifluoride may be charged to the reactor which is then heated to an operating temperature of about 325° C. and maintained thereat for a period of two hours. At the end of the two-hour period, charging of the phosphorus trifluoride to the autoclave may be discontinued and the autoclave may then be purged with nitrogen. After purging with nitrogen, heating may be discontinued and after the autoclave has returned to room temperature the excess pressure may be vented, the autoclave opened and the phosphorus fluoride-impregnated alumina recovered therefrom. The catalyst composition may then be calcined at a temperature of 500° C. in a nitrogen atmosphere for a period of two hours, following which the catalyst may then be used in oligomerization, alkylation, isomerization, etc. reactions.

I claim as my invention:

1. A hydrocarbon conversion process which comprises contacting a convertible hydrocarbon with a catalytic composition of matter comprising a phosphorus fluoride composited on a high surface area metal oxide support at conversion conditions, and recovering the resultant converted hydrocarbon.

2. The process as set forth in claim 1 in which said hydrocarbon conversion process is an alkylation process, said convertible hydrocarbons are benzene and propylene and said converted hydrocarbon is isopropylbenzene.

3. The process as set forth in claim 1 in which said high surface area metal oxide is an alumina.

4. The process as set forth in claim 3 in which said high surface area metal oxide is gamma-alumina.

5. The process as set forth in claim 3 in which said high surface area metal oxide is theta-alumina.

6. The process as set forth in claim 1 in which said phosphorus fluoride is phosphorus trifluoride.

7. The process as set forth in claim 1 in which said phosphorus fluoride is phosphorus pentafluoride.

8. A process for the oligomerization of butene-2 which comprises contacting the butene-2 with a phosphorus fluoride composited on a high surface area metal oxide support at oligomerization conditions, and recovering the resultant oligomer of butene-2.

9. A hydrocarbon conversion process which comprises contacting a convertible hydrocarbon with a catalytic composition of matter comprising phosphorus pentafluoride composited on gamma-alumina at conversion conditions, and recovering the resultant converted hydrocarbon.

* * * * *